United States Patent
Fechner et al.

(10) Patent No.: US 7,166,549 B2
(45) Date of Patent: Jan. 23, 2007

(54) ANTIMICROBIAL, ANTI-INFLAMMATORY, WOUND-HEALING AND DISINFECTING GLASS AND USE THEREOF

(75) Inventors: Jorg Hinrich Fechner, Moinz (DE); José Zimmer, Ingelheim (DE)

(73) Assignee: Schott AG, Mainz (DE)

(*) Notice: Subject to any disclaimer, the term of this patent is extended or adjusted under 35 U.S.C. 154(b) by 91 days.

(21) Appl. No.: 10/487,186

(22) PCT Filed: Aug. 17, 2002

(86) PCT No.: PCT/EP02/09217

§ 371 (c)(1), (2), (4) Date: Jun. 24, 2004

(87) PCT Pub. No.: WO03/018498

PCT Pub. Date: Mar. 6, 2003

(65) Prior Publication Data

US 2005/0064193 A1    Mar. 24, 2005

(30) Foreign Application Priority Data

| Aug. 22, 2001 | (DE) | ................ 101 41 116 |
| Nov. 20, 2001 | (DE) | ................ 101 56 577 |
| Mar. 27, 2002 | (DE) | ................ 102 13 630 |

(51) Int. Cl.
C03C 3/062 (2006.01)
C03C 3/097 (2006.01)
C03C 3/11 (2006.01)

(52) U.S. Cl. ............... 501/56; 501/57; 501/58; 501/59; 501/63; 501/65; 501/66; 501/67; 501/70; 501/72; 501/73; 501/77; 501/79

(58) Field of Classification Search ............ 501/57–59, 501/63, 65, 66, 67, 69, 70, 72, 73, 77, 79
See application file for complete search history.

(56) References Cited

U.S. PATENT DOCUMENTS

| 3,773,530 A * | 11/1973 | Morgan ................ 501/63 |
| 3,926,246 A | 12/1975 | Corbett et al. ........... 164/56 |
| 3,954,485 A * | 5/1976 | Seward et al. ............ 501/13 |
| 4,000,998 A * | 1/1977 | Rittler ................... 65/33.7 |
| 4,092,139 A | 5/1978 | Ference ............... 65/30 R |
| 4,567,104 A * | 1/1986 | Wu ..................... 428/410 |
| 5,034,353 A | 7/1991 | Shibuya et al. ............ 501/3 |
| 5,074,916 A | 12/1991 | Hench et al. ........... 106/35 |
| 5,290,544 A | 3/1994 | Shimono et al. ......... 424/63 |
| 5,639,702 A | 6/1997 | Imashita et al. ......... 501/44 |
| 5,807,641 A | 9/1998 | Oku et al. ............... 428/701 |
| 5,834,008 A | 11/1998 | Greenspan et al. ....... 424/443 |
| 6,074,984 A | 6/2000 | Demmel et al. ......... 502/439 |
| 6,123,743 A | 9/2000 | Carman et al. ............ 51/307 |
| 6,143,318 A | 11/2000 | Gilchrist et al. ......... 424/446 |
| 6,245,732 B1 | 6/2001 | Gallon ................. 510/507 |
| 2002/0086039 A1 | 7/2002 | Lee et al. .............. 424/401 |
| 2004/0137075 A1 | 7/2004 | Fechner et al. .......... 424/601 |
| 2004/0166172 A1 | 8/2004 | Rosati et al. |
| 2005/0064193 A1 | 3/2005 | Fechner et al. .......... 428/406 |
| 2005/0119105 A1 | 6/2005 | Zimmer et al. .......... 501/32 |

FOREIGN PATENT DOCUMENTS

| CN | 1323527 | 11/2001 |
| DE | 2800145 | 9/1978 |
| DE | 3939831 | 6/1990 |
| DE | 195 03 167 | 8/1996 |
| EP | 425927 | 5/1991 |
| EP | 0921105 | 6/1999 |
| GB | 1 294 337 | 10/1972 |
| JP | 3-146436 | 6/1991 |
| JP | 7-25635 | 1/1995 |
| JP | 07026635 | 1/1995 |
| JP | 7-291654 | 11/1995 |
| JP | 8-2452240 | 9/1996 |
| JP | 10-218637 | 8/1998 |
| JP | 10-231187 | 9/1998 |
| JP | 11-209143 | 8/1999 |
| JP | 11-228173 | 8/1999 |
| JP | 2000-203876 | 7/2000 |
| JP | 2000-264674 | 9/2000 |
| WO | WO96/21628 | 7/1996 |
| WO | WO 97/27148 | 7/1997 |
| WO | WO00/15167 | 3/2000 |
| WO | WO 00/38552 | 7/2000 |
| WO | WO00/66086 | 11/2000 |
| WO | WO00/76486 | 12/2000 |

OTHER PUBLICATIONS

U.S. Patent Application entitled Antimicrobial, Anti-Inflammatory, Wound Healing Glass Powder and Use Thereof, filed on Feb. 19, 2004.

* cited by examiner

*Primary Examiner*—David Sample
(74) *Attorney, Agent, or Firm*—Baker & Daniels

(57) ABSTRACT

The invention relates to an antimicrobial, anti-inflammatory and disinfecting glass, whereby the glass comprises: 30–95 wt. % $SiO_2$, 0–40 wt. % $Na_2O$, 0–40 wt. % $K_2O$, 0–40 wt. % $Li_2O$, 0–35 wt. % CaO, 0–10 wt. % MgO, 0–10 wt. % $Al_2O_3$, 0–15 wt. % $P_2O_5$ wt. % $B_2O_3$?, 0–10 wt. % NaF, 0–10 wt. % LiF, 0–10 wt. % KF, 0–10 wt. % $CaF_2$, 0–5 wt. % $Ag_2O$, 0–10 wt. % $MgF_2$, 0–2 wt. % $Fe_2O_3$ and 0–10 wt. % $XJ_y$, where X=Li, Na, K, Rb, Cs, Be, Mg, Ca, Sr, Ba, Ag or Zn and y=1 or y=2 and the sum of $XJ_y >$ is 10 ppm.

27 Claims, No Drawings

ANTIMICROBIAL, ANTI-INFLAMMATORY, WOUND-HEALING AND DISINFECTING GLASS AND USE THEREOF

The present invention relates to an antimicrobial, anti-inflammatory, wound-healing and disinfecting glass and a glass powder containing such a glass.

Glasses for biological or medical use which contain iodide or halides in general are known from the following patents:
German Patent 39 39 831
Japanese Patent 91146436
U.S. Pat. No. 5,807,641

German Patent 39 39 831 describes a crystalline glass or a glass ceramic, and especially a bio-compatible glass or a bio-compatible glass ceramic which is usable for the repair of the damaged or broken portion of a tooth. German Patent 39 39 831 provides for coloring using a dye, such as for example a noble metal halide. The halides were not however specified.

U.S. Pat. No, 5,807,641 identifies an antibacterial and anti-fungicidal glass composition for ceramic products, such as are known, for example, for sanitary materials, whereby the materials may contain a silver halide. The glasses described in U.S. Pat. No. 5,807,641 are used particularly as glazing materials.

Japanese Patent A-91146436 identifies a micro-biocidal glass for water treatment or elimination of algae and microorganisms in water. The glass according to Japanese Patent A-91148436 contains halides as raw material.

The object of the present invention is to make available an antimicrobial, anti-inflammatory and disinfecting glass which itself has an antimicrobial and anti-inflammatory effect and which benefits synergistically from the addition of iodide.

The object is achieved by means of iodide-containing glass compositions according to claim 1.

Iodine or iodide possesses an antimicrobial effect which has been exploited in the medical field for a long time. An iodide tincture is a clear brownish red liquid, which consists of 2.5 parts iodine, 2.5 parts potassium iodide, 28.5 parts water and 66.5 parts of 90% alcohol.

The small amount of iodide in the glass makes the present invention outstandingly suitable as a nutritional supplement. Glasses with higher quantities of iodide display a distinct antimicrobial effect as well as disinfecting and ant-inflammatory or wound healing properties, this effect synergisticaly exceeding the individual effects of the glasses and the iodide ions.

The glass contains between 30 and 80 wt % of $SiO_2$ as a network former. At lower concentrations the hydrolytic resistance creases markedly, so that the grindings can no longer be guaranteed not to dissolve significantly in aqueous media. At higher values the crystallization stability decreases and the working temperature is markedly increased, so that the molten and hot formability are impaired.

$Na_2O$ is introduced as a flux material during melting of the glass. At total concentrations of less than 5% the behavior of the melt is adversely affected. Furthermore, the necessary ion exchange mechanism is no longer sufficient to achieve antibacterial action. At concentrations higher than 40 wt % deterioration of the chemical stability or, as the case may be, resistance to hydrolysis is observed especially in connection with a decrease in the $SiO_2$ content.

$P_2O_5$ is a network former and can increase the crystallization stability. The concentrations should not be above 16 wt % as otherwise the chemical stability of silicate glasses decreases too strongly. $P_2O_5$ improves the surface stability of the glasses.

$B_2O_3$ is a network former and enhances the chemical stability. The reactivity of the glass and thereby its effectiveness may be controlled by varying its content.

CaO improves the chemical stability especially in the mildly alkaline range and is therefore necessary in order to prevent dissolution of the glass in aqueous media. Otherwise ion exchange with $H^+$ can take place.

MgO improves the chemical resistance in the mildly alkaline range and is therefore necessary so as to prevent dissolution of the glass in aqueous media. Moreover, ion exchange with $H^+$ can take place.

$K_2O$ and $Li_2O$ additions promote the interchangeability of sodium or potassium, and lithium can itself exchange with $H^+$ ions.

$Al_2O_3$ may be added up to a maximum amount of 10 wt % to increase the crystallization stability.

Fluoride may be added to achieve a synergistic reinforcement of the iodide activity.

The glass according to the present invention may be manufactured on a large scale using standard methods.

In a preferred embodiment the glass contains 30–60 wt % $SiO_2$, 2–40 wt % $Na_2O$, 5–40 wt % CaO, 1–15 wt % $P_2O_5$ and $XI_y$>100 ppm, whereby X, Li, Na, K, Rb, Cs, Be, Mg, Ca Sr, Ba, Ag, Zn and y=1 or y=2.

An especially preferred embodiment contains 30–60 wt % $SiO_2$, 5–35 wt % $Na_2O$, 2–10 wt % $P_2O_5$, and $XI_y$>100 ppm whereby X, Li, Na, K, Rb, Cs, Be, Mg, Ca, Sr, Ba, Ag, Zn and y=1 or y=2. To achieve a disinfecting effect the amount of $XI_y$ is preferred to be >500 ppm, especially >1 wt %, >2 wt % being especially preferred.

As a food supplement as well as for use inside the human body $XI_y$ contents of 10 ppm to 1 wt %, are preferred especially 10 ppm to 500 ppm, the especially preferred content being 10 ppm to 250 pm The glasses according to the present invention may also be obtained and products mixed in, in the form of powders. Therefore the glasses are advantageously suitable for grinding in different grinding media for example water, in other words the glass has adequate resistance to hydrolysis.

In addition to manufacturing by melt processes, alternative manufacturing methods by means of sol-gel or sintering are conceivable.

Particle sizes of <100 µm may be obtained by a grinding process. Particle sizes of less than 50 µm or 20 µm have proven to be convenient. Particle sizes of <10 µm as well as smaller than 5 µm are particularly suitable. Particle sizes of <1 µm were shown to be most suitable.

The grinding process may be carried out in aqueous and non-aqueous grinding media.

Mixtures of different glass powders from the range of compositions having different compositions and grain sizes are possible in order to combine specific effects.

The glasses that lie within the claimed composition ranges fulfill all requirements relative to their use in the areas of sanitary paper, cosmetics, dyes, lacquers, plasters, medicinal products, cosmetic applications, foodstuff additives as well as use in antiperspirants, for example deodorants.

The glass may be utilized in any suitable form including the mentioned powder form, mixtures of different powders from the range of compositions are likewise possible. Mixing with other glass powders is also possible in order to combine particular effects.

The invention is described below, with reference to exemplary embodiments.

EXEMPLARY EMBODIMENTS

A glass was melted from the raw materials then subsequently formed into ribbons. These ribbons were further processed by dry grinding to a powder with a particle size of d50–4 µm.

Table 1 presents compositions (synthesis values) [wt %] and properties of glasses according to the present invention.

TABLE 1

Glass Compositions

|  | Example 1 | Example 2 | Example 3 | Example 4 | Example 5 |
|---|---|---|---|---|---|
| $SiO_2$ | 44.5 | 45 | 55 | 45.0 | 71.2 |
| $Al_2O_3$ |  |  |  | 24.5 | 0.35 |
| CaO | 24.1 | 22.5 | 19.5 |  | 9.5 |
| MgO |  |  |  |  | 4.0 |
| $P_2O_5$ | 5.8 | 6 | 6 | 6 |  |
| $Na_2O$ | 24.1 | 22.5 | 19.4 | 23.5 | 13.0 |
| $K_2O$ |  |  |  |  | 0.05 |
| NaI | 1.2 | 2.0 | 0.1 | 1.0 | 1.1 |
| $CaI_2$ |  | 2.0 |  |  |  |
| AgI | 0.3 |  |  |  |  |
| $Fe_2O_3$ |  |  |  |  | 0.1 |

The antibacterial effects of the powders following Europ. Pharmakopoe ($3^{rd}$ edition) are shown for Exemplary Embodiment 1 in Table 2.

TABLE 2

Antibacterial Effect of Exemplary Embodiment 1:
Following European Pharmakopoe (Germ Strain Test).

|  | E. Coli. | F. Aeruginosa | S. Aureus | C. Albicans | A. Niger |
|---|---|---|---|---|---|
| Start | 0 | 0 | 0 | 0 | 0 |
| 2 Days | 0 | 0 | 0 | 0 | 0 |
| 7 Days | 0 | 0 | 0 | 0 | 0 |
| 14 Days | 0 | 0 | 0 | 0 | 0 |
| 21 Days | 0 | 0 | 0 | 0 | 0 |
| 28 Days | 0 | 0 | 0 | 0 | 0 |

The antimicrobial, anti-inflammatory, wound-healing and disinfecting glasses or glass powders according to the present invention may be added as a foodstuff supplement, in cosmetic production, antiperspirant production, in medicinal products, plastics and polymers, sanitary paper, dyes, and lacquers as well as plaster and purification means.

Ion Release into Water (after 24 h) for Exemplary Embodiment 1

|  | 0.01 wt % | 0.1 wt % | 1 wt % | 10 wt % |
|---|---|---|---|---|
| Si |  | 54 mg/L |  |  |
| Ca |  | 24 mg/L |  |  |
| P |  | 0.2 mg/L |  |  |
| Na |  | 31 mg/L |  |  |
| Ag |  | <1 ppm |  |  |
| I |  | <30 mg/L |  |  |

The invention claimed is:

1. An antimicrobial, anti-inflamatory and disinfecting glass, wherein the glass contains:
   30–60 wt % $SiO_2$
   2–40 wt % $Na_2O$
   0–40 wt % $K_2O$
   0–40 wt % $Li_2O$
   5–40 wt % CaO
   0–10 wt % MgO
   0–10 wt % $Al_2O_3$
   1–15 wt % $P_2O_5$
   0–5 wt % $B_2O_3$
   0–10 wt % NaF
   0–10 wt % LiF
   0–10 wt % KF
   0–10 wt % $CaF_2$
   0–5 wt % $Ag_2O$
   0–10 wt % $MgF_2$
   0–2 wt % $Fe_2O_3$
   0–10 wt % $XI_y$,
   where X is Li, Na, K, Rb, Cs, Be, Mg, Ca, Sr, Ba, Ag, Zn and y=1 or 2 and where the sum of $XI_y$ is >10 ppm.

2. The antimicrobial, anti-inflammatory and disinfecting glass, according to claim 1, wherein the sum of $Na_2O+K_2O+Li_2O \geqq 5$ wt %.

3. The antimicrobial, anti-inflammatory and disinfecting glass, according to claim 1, wherein the glass contains:
   5–35 wt % $Na_2O$
   2–10 wt % $P_2O_5$.

4. The glass of claim 1 wherein the sum of $XI_y$ is >100 ppm.

5. The glass of claim 1 wherein the sum of $XI_y$ is >500 ppm.

6. The glass of claim 1 wherein the sum of $XI_y$ is >1 wt %.

7. The glass of claim 1 wherein the sum of $XI_y$ is >2 wt %.

8. An antimicrobial, anti-inflammatory and disinfecting glass powder wherein the glass powder consists of a glass of composition as follows:
   30–60 wt % $SiO_2$
   2–40 wt % $Na_2O$
   0–40 wt % $K_2O$
   0–40 wt % $Li_2O$
   5–40 wt % CaO
   0–10 wt % MgO
   0–10 wt % $Al_2O_3$
   1–15 wt % $P_2O_5$
   0–5 wt % $B_2O_3$
   0–10 wt % NaF
   0–10 wt % LiF
   0–10 wt % KF
   0–10 wt % $CaF_2$
   0–5 wt % $Ag_2O$
   0–10 wt % $MgF_2$
   0–2 wt % $Fe_2O_3$
   0–10 wt % $XI_y$,
   where X is Li, Na, K, Rb, Cs, Be, Mg, Ca, Sr, Ba, Ag, Zn and y=1 or 2 and where the sum of $XI_y$ is >10 ppm.

9. The antimicrobial, anti-inflammatory and disinfecting glass powder, according to claim 8, wherein the glass particle size is $\leqq 100$ µm.

10. The antimicrobial, anti-inflammatory and disinfecting glass powder according to claim 8, wherein the particle size is $\leqq 20$ µm.

11. The glass of claim 8 wherein the particle size is $\leqq 10$ µm.

12. The antimicrobial, anti-inflammatory and disinfecting glass powder according to claim 8, wherein the glass particle size is <5 µm.

13. The antimicrobial, anti-inflammatory and disinfecting glass powder, according to claim 8, wherein the glass particle size is <1 µm.

14. The antimicrobial, anti-inflammatory and disinfecting glass powder, according to claim 8, as a food preserving additive and as a foodstuff supplement.

15. The antimicrobial, anti-inflammatory and disinfecting glass powder, according to claim 8, for use in cosmetic products.

16. The antimicrobial, anti-inflammatory and disinfecting glass powder, according to claim 8, for use in deodorant products.

17. The antimicrobial, anti-inflammatory and disinfecting glass powder, according claim 8, for use in antiperspiration means or antiperspirants.

18. The antimicrobial, anti-inflammatory and disinfecting glass powder, according to claim 8 for use in dyes and lacquers.

19. The antimicrobial, anti-inflammatory and disinfecting glass powder, according to claim 8 for use in medicinal products and preparations.

20. The antimicrobial, anti-inflammatory and disinfecting glass powder, according to claim 8 for use in plastics and polymers.

21. The antimicrobial, anti-inflammatory and disinfecting glass powder, according to claim 8 for use in sanitary paper.

22. The antimicrobial, anti-inflammatory and disinfecting glass powder, according to claim 8 for use in purification means.

23. The antimicrobial, anti-inflammatory and disinfecting glass powder, according to claim 8 for use in the field of medicine.

24. The antimicrobial, anti-inflammatory and disinfecting glass powder according to claim 8, for use in the care of wounds.

25. The antimicrobial, anti-inflammatory and disinfecting glass powder, according to claim 8 for use in dental medicine.

26. The antimicrobial, anti-inflammatory and disinfecting glass powder, according to claim 8 for use in the field of dental medicine as an antimicrobial and disinfecting additive in dental hygiene.

27. The antimicrobial, ant-inflammatory and disinfecting glass powder, according to claim 8 for use in the field of dental medicine as an anti-inflammatory additive for avoidance of gum bleeding.

* * * * *

UNITED STATES PATENT AND TRADEMARK OFFICE
CERTIFICATE OF CORRECTION

| | | |
|---|---|---|
| PATENT NO. | : 7,166,549 B2 | Page 1 of 1 |
| APPLICATION NO. | : 10/487186 | |
| DATED | : January 23, 2007 | |
| INVENTOR(S) | : Jorg Ginrich Fechner et al. | |

It is certified that error appears in the above-identified patent and that said Letters Patent is hereby corrected as shown below:

On Title Page

Item (75) Inventors: delete [Moinz] and insert --Mainz--

Signed and Sealed this

Seventeenth Day of April, 2007

JON W. DUDAS
*Director of the United States Patent and Trademark Office*